(12) United States Patent
Hinkle et al.

(10) Patent No.: US 11,708,380 B2
(45) Date of Patent: Jul. 25, 2023

(54) SELECTIVE ALKYLATION OF CYCLOPENTADIENE

(71) Applicant: ENTEGRIS, INC., Billerica, MA (US)

(72) Inventors: Paul Hinkle, Wallingford, PA (US); Scott A. Laneman, Vernon Hills, IL (US); Victoria Weidner, Media, PA (US)

(73) Assignee: ENTEGRIS, INC., Billerica, MA (US)

( * ) Notice: Subject to any disclaimer, the term of this patent is extended or adjusted under 35 U.S.C. 154(b) by 77 days.

(21) Appl. No.: 17/507,004

(22) Filed: Oct. 21, 2021

(65) Prior Publication Data

US 2022/0127294 A1 Apr. 28, 2022

Related U.S. Application Data

(60) Provisional application No. 63/104,234, filed on Oct. 22, 2020.

(51) Int. Cl.
*C07F 3/02* (2006.01)
*C07C 1/32* (2006.01)
*C07F 17/00* (2006.01)

(52) U.S. Cl.
CPC .............. *C07F 3/02* (2013.01); *C07C 1/326* (2013.01); *C07F 17/00* (2013.01)

(58) Field of Classification Search
None
See application file for complete search history.

(56) References Cited

U.S. PATENT DOCUMENTS

| | | |
|---|---|---|
| 3,255,267 A | 6/1966 | Fritz |
| 5,012,023 A | 4/1991 | Venier |
| 5,144,095 A | 9/1992 | Venier |
| 6,175,027 B1 | 1/2001 | Sullivan |
| 7,579,415 B2 | 8/2009 | Agapiou |
| 7,834,228 B1 | 11/2010 | Voll Barclay |
| 8,975,427 B2 | 3/2015 | Harlan |
| 2013/0085289 A1 | 4/2013 | Harlan |

FOREIGN PATENT DOCUMENTS

| | | |
|---|---|---|
| JP | 1025258 A | 1/1998 |
| JP | 2001097895 A | 4/2001 |
| JP | 2001097896 A | 4/2001 |
| JP | 2004285028 A | 10/2004 |
| WO | 2005033120 A1 | 4/2005 |
| WO | 2005033129 A1 | 4/2005 |

OTHER PUBLICATIONS

Chemical Abstract compound, STNext., RN 155640-60-1 (Entered STN: Jun. 9, 1994).
Cheng et al., C—C and C-X coupling reactions of unactivated alkyl electrophiles using copper catalysis., Chemical Society Reviews., vol. 49 No. 22., pp. 8036-8064., 2020.
Frankland et al., Alkaline-earth-metal arenesulfonates as precursors to organic derivatives of Group 2 metals., Journal of the Chemical Society., Dalton Transactions., vol. 22., pp. 4151-4152, 1996.
Reetz et al.; Metal, ligand and protective group tuning as a means to control selectivity. Pure & Applied Chemistry, (1992), 64, No. 3, 351-359.
Reetz et al.; Ligand Effects in Grignard Additions, Angew. Chem. Int. Engl. 31 (1992), 342-344.
Riemschneider et al; Substitution products of cyclopentadiene, 5th middle: ~ 1- and 2-tert-butylcycloentadienel; University of Berlin-Dahlem; 1959, pp. 1-7.
Sai et al.; Copper-Catalyzed Reaction of Alkyl Halides with Cyclopentadienylmagnesium Reagent; Organic Letters, vol. 10, No. 12, Apr. 2008, 2545-2547.
Stille et al.; "Intramolecular Diels-Alder Reaction of α,β-Unsaturated Ester Dienophiles with Cyclopentadiene and the Dependence on Tether Length"; J. Org Chem., vol. 54, No. 2, 1989, 434-444.

*Primary Examiner* — Joseph R Kosack

(57) ABSTRACT

Provided is a process for the mono-alkylation of cyclopentadiene, utilizing a cyclopentadiene magnesium halide and a metal salt of an alkyl or aryl sulfonate as co-reactant with an alkyl halide alkylating reactant. The process provides facile methodology for the mono-alkylation of cyclopentadiene, with conversions as high as about 96 percent and selectivity for mono-alkylation (over higher level alkylation, such as di- or tri-) as high as about 99%.

13 Claims, No Drawings

SELECTIVE ALKYLATION OF CYCLOPENTADIENE

CROSS-REFERENCE TO RELATED APPLICATIONS

This application claims the benefit under 35 USC 119 of U.S. Provisional Patent Application No. 63/104,234 filed Oct. 22, 2020, the disclosure of which is hereby incorporated herein by reference in its entirety.

TECHNICAL FIELD

The present disclosure relates to methodology for the selective mono-alkylation of cyclopentadiene.

BACKGROUND

Cyclopentadienes are useful as intermediates to many other useful organic compounds. Certain alkyl-substituted cyclopentadienes are useful as synthetic lubricants. (See, for example, U.S. Pat. Nos. 5,144,095 and 5,012,022). Additionally, the cyclopentadiene structure can also be found in many of the so-called single site metallocene catalysts used to make certain polyolefins such as polyethylenes and polypropylenes. (See, for example, U.S. Pat. No. 7,579,415).

One inherent difficulty in the handling of cyclopentadiene is that it tends to dimerize via a Diels-Alder reaction. This dimerization proceeds at room temperature over a period of hours, but can be reversed by utilization of heating, which in some cases requires a cracking procedure. Additionally, when attempting to make alkyl-substituted cyclopentadiene structures, the formation of di- and tri-alkyl species further complicates the synthetic regime by reducing yields and necessitating further purification.

Thus, a need exists for improved methodology for the mono-alkylation of cyclopentadiene structures.

SUMMARY

In summary, the disclosure relates to an improved process for monoalkylation of cyclopentadiene. In this process, cyclopentadienyl magnesium halide is reacted with a compound of the formula $MO_3SR'$, wherein M is chosen from alkali metals and alkaline earth metals, and R' is $C_1$-$C_8$ alkyl; phenyl; or phenyl substituted with one or more $C_1$-$C_8$ alkyl groups or phenyl. This step is believed to form a reactive intermediate in situ, which thus reacts with an alkyl halide of the formula R-X' to provide a compound of Formula (I):

wherein R is chosen from $C_1$-$C_8$ alkyl.

The process thus provides facile methodology for the mono-alkylation of cyclopentadiene, with conversions of at least about 96% and selectivity for mono-alkylation (over higher level alkylation, such as di- or tri-) at least about 99%.

DETAILED DESCRIPTION

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The term "about" generally refers to a range of numbers that is considered equivalent to the recited value (e.g., having the same function or result). In many instances, the term "about" may include numbers that are rounded to the nearest significant figure.

Numerical ranges expressed using endpoints include all numbers subsumed within that range (e.g., 1 to 5 includes 1, 1.5, 2, 2.75, 3, 3.80, 4 and 5).

In a first aspect, the disclosure is a process for preparing a compound of Formula (I):

wherein R is chosen from $C_1$-$C_8$ alkyl, the process comprising contacting (A) the reaction product of (a) a compound of the formula:

wherein X is chloro or bromo, and (b) a compound of the formula $MO_3SR'$,
wherein M is chosen from alkali metals and alkaline earth metals, and R' is $C_1$-$C_8$ alkyl; phenyl; or phenyl substituted with one or more $C_1$-$C_8$ alkyl groups or phenyl; and (B) a compound of the formula R-X', wherein X' is chosen from chloro, bromo, iodo, or alkyl- or aryl-sulfonate.

In one embodiment, R is isopropyl.

In one embodiment, M is chosen from alkaline earth metals.

In one embodiment, M is chosen from alkali metals.

In another embodiment, M is chosen from sodium, lithium, or potassium.

In certain embodiments, R' is chosen from trifluoromethyl, p-methylphenyl, or 1,3,5-trimethylphenyl.

In certain embodiments, the alkyl-sulfonate is chosen from $C_1$-$C_6$ alkyl sulfonates; in other embodiments, the aryl-sulfonate is phenyl sulfonate.

Advantageously, the process of the disclosure can be conducted to prepare mono-alkylated products in high yield and high-selectivity (for mono-alkylation). We have found that the utilization of a co-reactant of the formula $MO_3SR'$ results in the mono-alkylation of cyclopentadiene-type structures with conversions of at least about 70, 75, 80, 85, 90, or 96% and with selectivity for mono-alkylation at least about 70, 75, 80, 85, 90, 95, or 99%. Accordingly, the product so produced is also substantially devoid of bis-alkylated by-products, thereby allowing the direct product of the process to be utilized in further reactions with minimal processing.

The process may be conducted in polar aprotic solvents such as ethers. Exemplary ethers include dimethyl ether; diethyl ether; tetrahydrofuran; 2-methyltetrahydrofuran; 3-methyltetrahydrofuran; 1,4-dioxane; methyl t-butyl ether; methyl n-butyl ether; and the like. The process may be run at room temperature or elevated temperatures, for example from about 23° C. to about 60° C., and at atmospheric pressure.

In this reaction, we believe that the compound of the formula R-X' reacts with a reactive intermediate species which is itself the reaction product of (i) a compound of the formula CpMgX (Cp=cyclopentadiene) and (ii) a compound of the formula $MO_3SR'$. In this regard, we believe that this intermediate reactive species has the formula

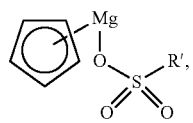

wherein R' is chosen from $C_1$-$C_8$ alkyl, phenyl, or phenyl substituted with one or more of $C_1$-$C_8$ alkyl or phenyl, which thereafter advantageously reacts with the compound of the formula R-X' to provide the monoalkylated products of Formula (I).

Accordingly, in another aspect, the disclosure provides an intermediate reactive species having the formula

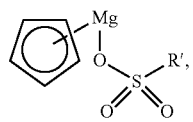

wherein R' is chosen from $C_1$-$C_8$ alkyl, phenyl, or phenyl substituted with one or more of $C_1$-$C_8$ alkyl or phenyl.

EXAMPLES

Preparation of Cyclopentadiene Magnesium Chloride

Cyclopentadiene magnesium chloride can be prepared from methylmagnesium chloride and cyclopentadiene using the methodology described in U.S. Pat. No. 6,175,027, incorporated herein by reference.

NMR (1H-NMR, protonated THF, internal standard 1,5-cyclooctadiene): 6.01 ppm (5H, b, Cp-H), 2.75 ppm (2H, b, residual Cp-CH$_2$), 0.2 ppm (4H, b, CH$_4$ generated from reaction), −2.06 ppm (3H, b, excess MeMgCl).

Example 1

CpMgCl solution (1.0M; 50 mL, 50 mmol) and sodium p-toluenesulfonate (9.71 g, 50 mmol) were reacted at 55° C. for several hours (2-6). The reaction mixture was then cooled to ambient temperature and neat isopropyl bromide (6.76 g, 55 mmol) was added slowly to the slurry. The reaction was monitored by GC over 20 hrs and the data in shown Table 1 below.

Example 2

CpMgCl (1.0M; 65 mL, 65 mmol) was heated to 60° C. and transferred over ten minutes onto isopropyl bromide (7.86 g, 64 mmol) and THF (1.83 g, 25 mmol), also at 60° C. The reaction was reflux at 65° C. for 4 hours and monitored by GC over 1 day and the data in Table 1.

The data in Table 1 shows the addition of tosylate to the reaction of CpMgCl and iPrBr substantially increase the conversion at 4 hr, as well as eliminating the formation of the iPr2Cp byproduct.

Example 3

CpMgCl solution (1.0M; 50 mL, 50 mmol) and sodium p-toluenesulfonate (9.71 g, 50 mmol) were reacted at 55° C. for several hours (2-6). The reaction mixture was then cooled to ambient temperature and neat butyl bromide (7.54 g, 55 mmol) slowly added to the slurry. The reaction was monitored by GC over 20 hrs and the data is shown in Table 2.

Example 4

CpMgCl solution (1.0M; 50 mL, 50 mm) was cooled to ambient temperature and neat butyl bromide (7.54 g, 55 mmol) slowly added to the clear solution. The reaction was monitored by GC over 20 hrs and the data is shown in Table 2.

The data in Table 2 shows the addition of tosylate to the reaction of CpMgCl and nBuBr provides a modest increase in conversion after 4 hr.

Rate Enhancement:

TABLE 1

Reactant and product values (from GC) at 4 hr in the synthesis of iPrCp

|  | % Cp | % iPrCp | % iPr$_2$Cp |
| --- | --- | --- | --- |
| Tosylate | 2.25 | 87.87 | 0 |
| without tosylate | 24.32 | 33.30 | 0.82 |

TABLE 2

Reactant and product values (from GC) at 4 hr in the synthesis of nBuCp

|  | % Cp | % nBuCp | % nBu$_2$Cp |
| --- | --- | --- | --- |
| 4 hr-tosylate | 0.82 | 93.71 | 0 |
| 4 hr-without tosylate | 8.17 | 80.30 | 0 |

Example 5

CpMgCl solution (1.0M; 1 L, 1 mol) and sodium p-toluenesulfonate (194 g, 1 mol) were reacted at 55° C. for several hours (2-6). The reaction mixture was then cooled to 10° C. and neat isopropyl bromide (135.3 g, 1.1 mol) slowly added to the slurry. The reaction was monitored by GC until the amount of free Cp relative to product was less than 5%. At completion, it was quenched by transferring to a solution in 1.5 eq hydrocarbon and dilute acetic acid. The organic layer was separated and washed with sodium carbonate. Low boiling compounds were then removed to yield a solution of 10-20% isopropylcyclopentadiene in THF/hydrocarbon. Solution analysis of this solution found <0.1% Cp and <0.1% iPr2Cp relative to iPrCp.

NMR (1H, C6D6): 1.08 ppm (6H, d, isopropyl CH$_3$), 2.62 ppm (1H, m, isopropyl CH), 2.82 ppm (2H, b, Cp-CH$_2$), 5.85-6.5 (5H, m, Cp-H)

Residual isopropyl bromide: 1.62 ppm (6H, d), 4.25 ppm (1H, m)

Aspects

In a first aspect, the disclosure provides a process for preparing a compound of Formula (I):

(I)

wherein R is chosen from $C_1$-$C_8$ alkyl, the process comprising contacting (A) the reaction product of (a) a compound of the formula:

wherein X is chloro or bromo, and (b) a compound of the formula $MO_3SR'$,
wherein M is chosen from alkali metals and alkaline earth metals, and R' is $C_1$-$C_8$ alkyl, phenyl, or phenyl substituted with one or more $C_1$-$C_8$ alkyl groups or phenyl; and (B) a compound of the formula R-X', wherein X' is chosen from chloro, bromo, iodo, alkyl-sulfonate, or aryl-sulfonate to produce the compound of Formula (I).

In a second aspect, the disclosure provides the process of the first aspect, wherein R is isopropyl.

In a third aspect, the disclosure provides the process of the first aspect, wherein R is sec-butyl.

In a fourth aspect, the disclosure provides the process of the first, second, or third aspect, wherein M is chosen from sodium, lithium or potassium.

In a fifth aspect, the disclosure provides the process of any one of the first through fourth aspects, wherein R' is 1,3,5-trimethylphenyl.

In a sixth aspect, the disclosure provides the process of any one of the first through fourth aspects, wherein R' is trifluoromethyl.

In a seventh aspect, the disclosure provides the process of any one of the first through fourth aspects, wherein R' is p-methylphenyl.

In an eight aspect, the disclosure provides the process of any one of the first through seventh aspects, wherein the compound of Formula (I) is produced with a conversion of at least about 70, 80, 90, or 96 percent.

In a ninth aspect, the disclosure provides the process of any one of the first through the eighth aspects, wherein the compound of Formula (I) is produced with a conversion of up to about 96 percent.

In a tenth aspect, the disclosure provides a compound of the formula

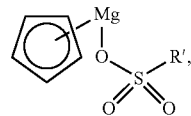

wherein R' is chosen from $C_1$-$C_8$ alkyl; phenyl; or phenyl substituted with one or more $C_1$-$C_8$ alkyl groups or phenyl.

In an eleventh aspect, the disclosure provides a compound according to the tenth aspect, wherein R' is chosen from 1,3,5-trimethylphenyl, trifluoromethyl, or 4-methylphenyl.

In a twelfth aspect, the disclosure provides a compound according to the tenth or eleventh aspect, wherein R' is 4-methylphenyl.

In a thirteenth aspect, the disclosure provides a compound according to the tenth or eleventh aspect, wherein R' is 1,3,5-trimethylphenyl.

In a fourteenth aspect, the disclosure provides a compound according to the tenth or eleventh aspect, wherein R' is trifluoromethyl.

Having thus described several illustrative embodiments of the present disclosure, those of skill in the art will readily appreciate that yet other embodiments may be made and used within the scope of the claims hereto attached. Numerous advantages of the disclosure covered by this document have been set forth in the foregoing description. It will be understood, however, that this disclosure is, in many respects, only illustrative. The disclosure's scope is, of course, defined in the language in which the appended claims are expressed.

What is claimed is:

1. A process for preparing a compound of Formula (I):

(I)

wherein R is chosen from $C_1$-$C_8$ alkyl, the process comprising contacting (A) the reaction product of (a) a compound of the formula:

wherein X is chloro or bromo, and (b) a compound of the formula $MO_3SR'$, wherein M is chosen from alkali metals or alkaline earth metals, and R' is $C_1$-$C_8$ alkyl, phenyl, or phenyl substituted with one or more $C_1$-$C_8$ alkyl groups or phenyl; and (B) a compound of the formula R-X', wherein X' is chosen from chloro, bromo, iodo, alkyl-sulfonate, or aryl-sulfonate, to produce the compound of Formula (I).

2. The process of claim 1, wherein R is isopropyl.

3. The process of claim 1, wherein R is sec-butyl.

4. The process of claim 1, wherein M is chosen from sodium, lithium or potassium.

5. The process of claim 1, wherein R' is 1,3,5-trimethylphenyl.

6. The process of claim 1, wherein R' is trifluoromethyl.

7. The process of claim 1, wherein R' is p-methylphenyl.

8. The process of claim 1, wherein the compound of Formula (I) is produced with a conversion of at least about 70 percent.

9. A compound of the formula

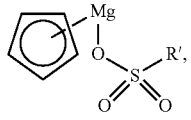

wherein R' is chosen from $C_1$-$C_8$ alkyl, phenyl, or phenyl substituted with one or more $C_1$-$C_8$ alkyl groups or phenyl.

10. The compound of claim 9, wherein R' is chosen from 1,3,5-trimethylphenyl, trifluoromethyl, or 4-methylphenyl.

11. The compound of claim 9, wherein R' is 4-methylphenyl.

12. The compound of claim 9, wherein R' is 1,3,5-trimethylphenyl.

13. The compound of claim 9, wherein R' is trifluoromethyl.

* * * * *